(12) United States Patent
Idowu et al.

(10) Patent No.: US 10,610,402 B1
(45) Date of Patent: Apr. 7, 2020

(54) STOMA PROLAPSE PROSTHESIS

(71) Applicants: Olajire Idowu, Lodi, CA (US);
Sunghoon Kim, San Ramon, CA (US)

(72) Inventors: Olajire Idowu, Lodi, CA (US);
Sunghoon Kim, San Ramon, CA (US)

( * ) Notice: Subject to any disclaimer, the term of this patent is extended or adjusted under 35 U.S.C. 154(b) by 0 days.

(21) Appl. No.: 15/732,390

(22) Filed: Nov. 3, 2017

(51) Int. Cl.
*A61F 5/445* (2006.01)
*A61F 5/44* (2006.01)

(52) U.S. Cl.
CPC ............ *A61F 5/445* (2013.01); *A61F 5/4404* (2013.01); *A61F 2005/4455* (2013.01)

(58) Field of Classification Search
CPC . A61B 17/02; A61B 17/3423; A61B 17/0293; A61B 17/0218; A61B 17/3431; A61B 2017/3492; A61B 17/0057; A61B 2017/3452; A61B 2017/00641; A61B 2017/345; A61F 5/445; A61F 5/44; A61F 2/82
See application file for complete search history.

(56) References Cited

U.S. PATENT DOCUMENTS

| 2,563,597 | A | | 8/1951 | Friedman |
| 3,447,533 | A | * | 6/1969 | Spicer ..................... A61F 5/445 215/358 |
| 9,398,871 | B2 | | 7/2016 | Idowu et al. |
| 2010/0163054 | A1 | * | 7/2010 | Breznel ............ A61B 17/12022 128/831 |
| 2015/0126946 | A1 | | 5/2015 | Fernandez et al. |
| 2015/0141944 | A1 | | 5/2015 | Hanuka et al. |
| 2015/0173938 | A1 | | 6/2015 | Brant et al. |
| 2015/0313598 | A1 | * | 11/2015 | Todd ................... A61B 17/1114 606/153 |

* cited by examiner

*Primary Examiner* — Christine H Matthews
(74) *Attorney, Agent, or Firm* — Robert Charles Hill

(57) ABSTRACT

A stoma-prolapse prosthesis includes a single plastic piece configured as two flexible open rings with spokes tied together at their centers by a central stem. When in place for use, one of the two flexible open rings is collapsed between the fingers and inserted inside the stoma and pushed through to the interior of the abdominal wall. The central stem is sized to be just long enough to match the thickness of the abdominal wall around the stoma. The other of the two flexible open rings self-locks around the perimeter of the stoma on the outside skin surface. The inside one of the two flexible open rings takes up the tissue slack caused by the prolapse, and the spokes inside block the bowel tissues from pushing through.

9 Claims, 3 Drawing Sheets

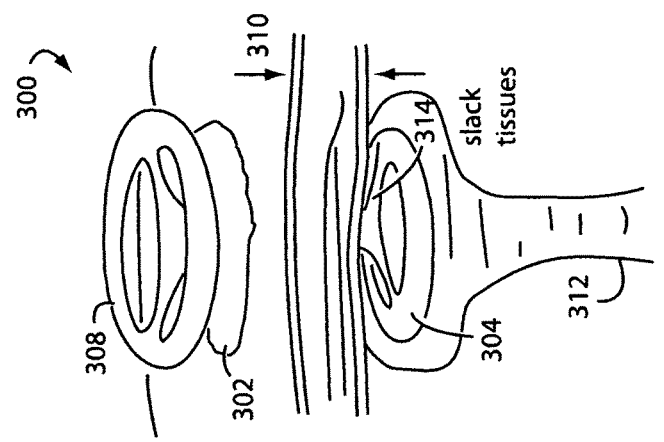
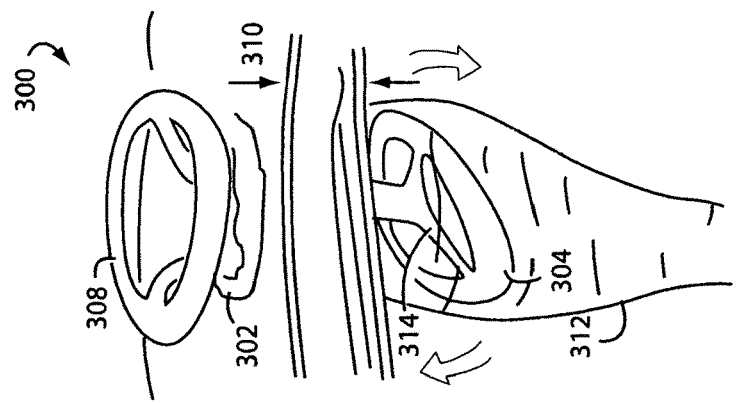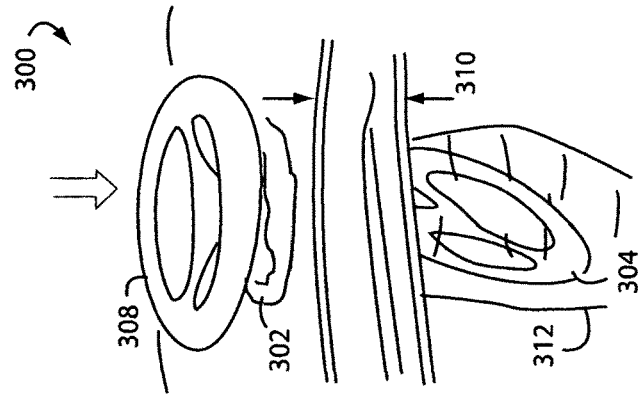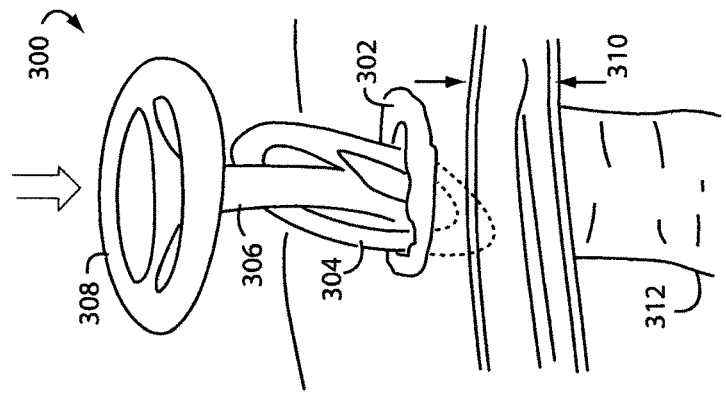

STOMA PROLAPSE PROSTHESIS

FIELD OF INVENTION

The present invention relates to a stoma-prolapse prosthesis, and more specifically to devices that can be inserted into an abdominal stoma to control and support prolapse of the small bowel and colon through the abdominal wall.

BACKGROUND

Various kinds of infirmaries of the human bowel can result in a surgical intervention in which the intestine is cut and one end is brought out through an artificial opening in the abdominal wall called a stoma. Such stoma surgery thereafter requires the use of a replaceable ostomy bag to collect fecal mater otherwise passing normally from the colon.

Once the surgery around the stoma has healed, too large of a surgical opening in the abdominal wall, chronic coughing, obesity, ordinary peristalsis of the bowel, and stool passing can cause pressures inside the abdomen to development around the stoma to stretch the tissues and progressively prolapse the stoma through the abdominal wall. The severity of prolapse can vary from a relatively small 2-3 centimeters to a large 10+ centimeter prolapse. If not too severe, such prolapse can be conservatively managed without resorting to more surgery to address the prolapse. If intervened early with an effective prosthesis, advancing prolapse can be halted.

Three common ostomies that can prolapse are a colostomy, an ileostomy and an urostomy. Various prosthesis to control and support stoma prolapse of these sort have been developed, but none proven to be completely satisfactory.

U.S. Pat. No. 9,378,871 82 by the present inventors discloses devices, systems and methods for containing and monitoring an exposed gestrointrotinal body part of a patient. Gastroschisis addressed in the reference and stoma prolapse addressed in the present invention are two different diseases which require different devices to mage them. The surgical pouch or silo of the reference has one ring which is placed inside the abdominal cavity. In contrast, the stoma prolapse prosthesis of the present invention has one open ring placed in the lumen of the bowel and another open ring placed outside the abdominal wall in the stoma. These two open ring components are joined with a connecting segment which traverses through the opening of the stoma.

SUMMARY

Briefly, stoma-prolapse prosthesis embodiments of the present invention include a single plastic piece configured as two flexible open rings with spokes linked together at their centers by a central stem. When in place for use, one of the two flexible open rings is collapsed between the fingers and inserted inside the stoma and pushed through to the interior of the abdominal wall. The central stem is sized to be just long enough to match the thickness of the abdominal wall around the stoma. The other of the two flexible open rings stops around the perimeter of the stoma on the outside skin surface. The inside one of the two flexible open rings takes up the tissue slack caused by the prolapse, and the spokes inside block the bowel tissues from pushing through.

THE DRAWINGS

FIGS. 3A-3D are a series of perspective view diagrams and a cutaway of the abdomen near a stoma subject to prolapse, and FIG. 3A shows the initial insertion in a first step, FIG. 3B shows the stoma-prolapse prosthesis nearly fully inserted, FIG. 3C shows the inside open ring of the stoma-prolapse prosthesis returning to its parallel and fully round condition, and FIG. 3D shows the stoma-prolapse prosthesis fully inserted and fully seated in its normal service condition.

DETAILED DESCRIPTION OF THE EMBODIMENTS

Figure 1:
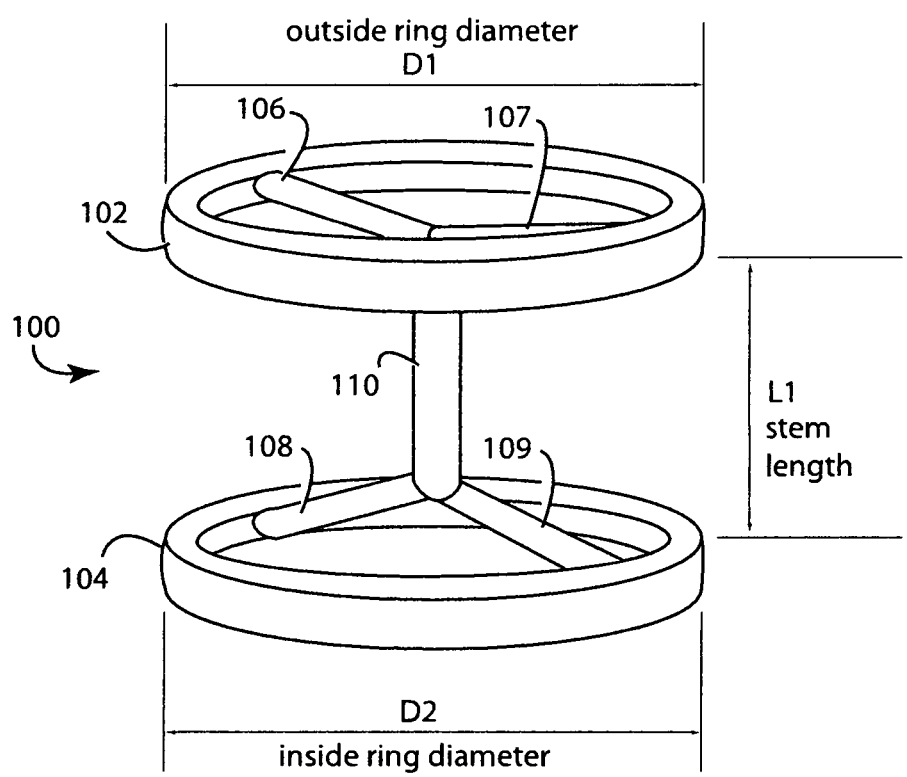
FIG. 1 is a perspective diagram of a stoma-prolapse prosthesis embodiment of the present invention.

FIG. 1 represents a stoma-prolapse prosthesis in an embodiment of the present invention, and is referred to herein by general reference numeral 100. The stoma-prolapse prosthesis 100 includes, in a single biocompatible plastic piece, two flexible open rings 102 and 104 configured with spokes 106-109 linked together at their centers by a central stem 110. The two flexible open rings 102 and 104 are generally parallel to one another and coaxial on the central stem 110. In one embodiment, the two flexible open rings 102 and 104 are fashioned from quarter-inch latex and non-latex surgical tubing into loops about two inches in outside diameter (D1 and D2), and the central stem 110 is also quarter-inch latex and non-latex surgical tubing with a length (L1) of about one inch and fused to the spokes of the two flexible open rings 102 and 104.

One objective of stoma-prolapse prosthesis 100 is to thwart stoma prolapse with minimal interference both to the attachment of a standard appliance and to fecal discharge. The construction should be smooth with no sharp corners or crevices, and use biocompatible materials that are readily cleaned and sterilized.

The two flexible open rings 102 and 104 must be made of a material that has sufficient elastic memory strength and resiliency to balloon the prolapse tissue lumen while still inside the abdomen, and yet the material must not be so inflexible that open ring cannot be readily collapsed and twisted between fingers to be inserted or withdrawn from the intended stoma. Stomas will vary in size from one user to the next, and the dimensions of 100 should be adjusted in accordance for a good fit and proper function.

The two flexible open rings 102 and 104 need not be the same diameters (D1, D2), but if they are, either could then serve as the one used for insertion inside the stoma.

The plastics in medical devices are regulated like any other materials that may come in contact with human tissue or fluids, and such usually falls under testing procedures issued under U.S. Pharmacopeial Convention (USP) Reference Standards or ISO-10993. The approved use of biocompatible devices in such contact has three timescale classifications, limited: less than 24-hour exposure; prolonged: 24-hours to thirty day exposure; and permanent: thirty days or longer.

Devices approved for biocompatibility are also further categorized as, (a) surface devices such as electrodes for monitoring, contact lenses, catheters, endotracheal tubes, sigmoidoscopes, etc.; (b) externally communicating devices such as laprascopes, blood administration devices, pacemakers, oxygenators etc.; and (c) implant devices such as orthopedic pins or plates, heart valves, grafts, stents, etc. Biocompatible devices submitted for approval are subjected to mechanical, thermal, and chemical tests, as well as implantation, systemic injection, and intracutaneous injection. Typical materials for biocompatible applications include medical grades of polyvinylchloride (PVC) and polyethylene, polyether ether ketone (PEEK), polycarbonate, Ultem® amorphous thermoplastic polyetherimide (PEI) resins, polysulfone, polypropylene, polyurethane, and silicone.

Figure 2A:
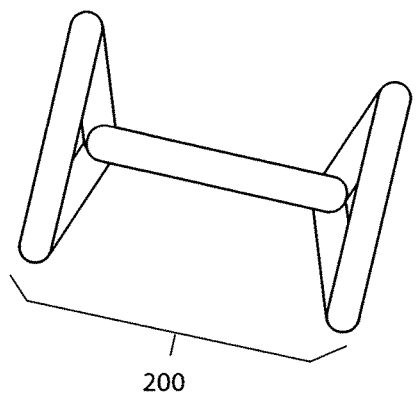
FIGS. 2A and 2B are cross sectional side view diagrams of the process for installing the stoma-prolapse prosthesis of FIG. 1, and they show the fit inside a typical stoma in the abdomen.
Figure 2A:
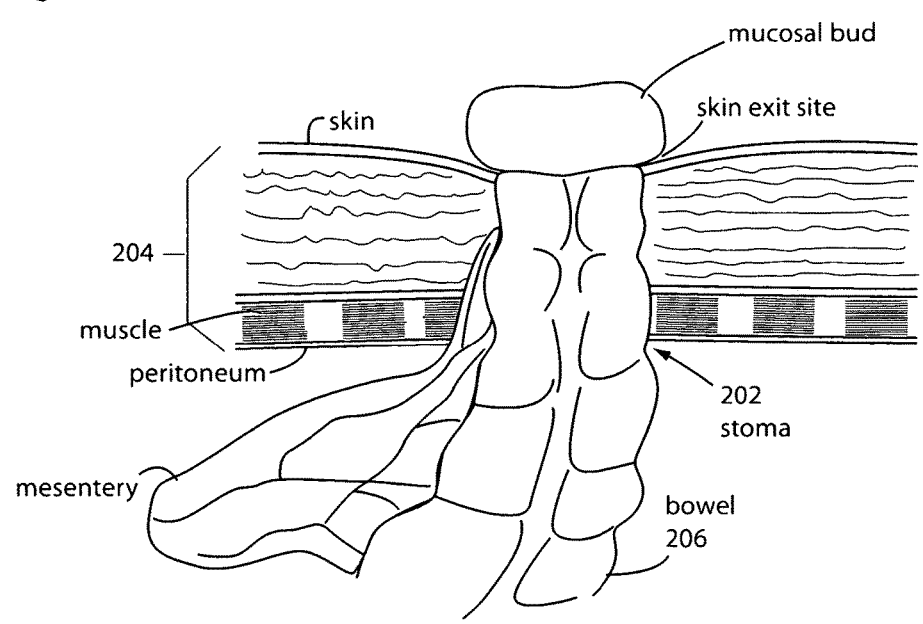
Figure 2B:
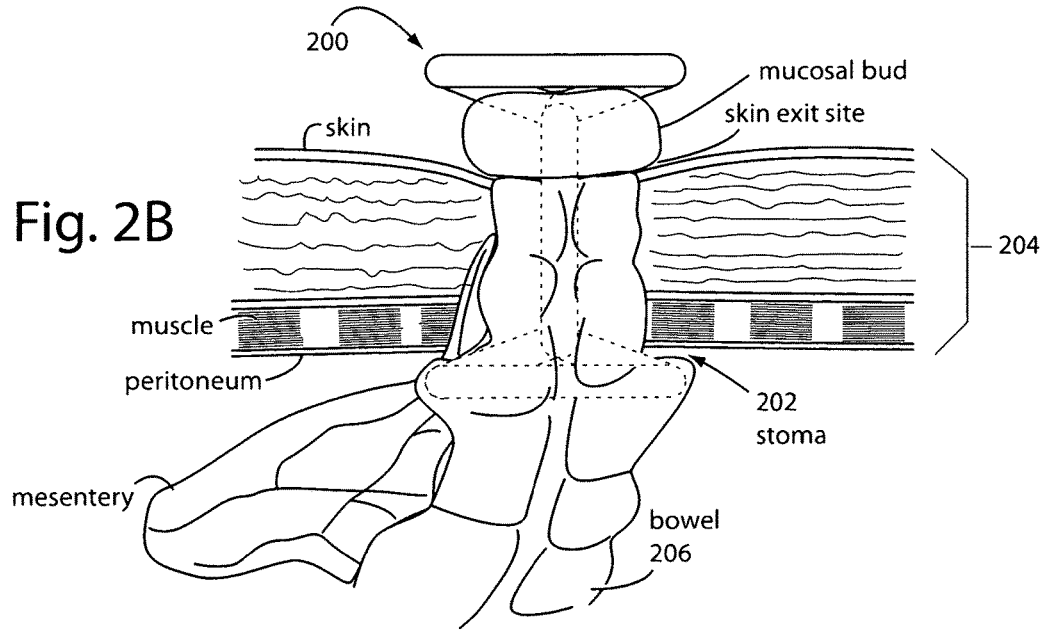

FIGS. 2A and 2B show a stoma-prolapse prosthesis 200 before and after insertion into a stoma 202. When in place, the stoma-prolapse prosthesis 200 is dimensioned to span through the thickness of the abdominal wall 204 at a stoma exit site. The stoma-prolapse prosthesis 200 balloons the lumen of the bowel 206 out to seat itself in place. However, the material of the stoma-prolapse prosthesis 200 is flexible enough so that it can be unseated and pulled back out with moderate force.

FIGS. 3A-3D illustrate the steps needed by the user to insert a stoma-prolapse prosthesis 300 into a stoma 302. In FIG. 3A, a first open ring 304 of two flexible open rings is collapsed into a thin oval between the fingers and inserted down inside the stoma 302. In FIG. 3B, a now collapsed open ring 304 is pushed by a stem 306 (FIG. 3A). Stem 306 is linked to the second flexible open ring 308 through to the interior of an abdominal wall and peritoneum 310 and the lumen of a bowel 312. The center stem 306 is sized to be long enough to exceed the thickness of the abdominal wall around the stoma.

FIG. 3C shows stoma-prolapse prosthesis 300 after being slipped in further. The second flexible open ring 308 fits around the perimeter of the stoma 302 on the skin surface and prevents the whole assembly from slipping down into a user's body. FIG. 3D is meant to illustrate the seating of first flexible open ring 304 into a parallel orientation on stem 306 (FIG. 3A) with second flexible open ring 308. The first flexible open ring 304 seats in place and takes up tissue slack caused by the prolapse. A pair of spokes 314 on first flexible open ring 304 also act as stoppers to prevent the prolapse from rolling up and through the inside of stoma 302.

The invention claimed is:

1. A method of managing abdominal stoma prolapse, comprising:
    inserting a prosthesis partially into an abdominal stoma;
    compressing and deforming, before the inserting, a distal end of the prosthesis manually such that it will fit through into the abdominal stoma;
    seating the prosthesis inside the stoma; and
    moving fecal matter through the prosthesis.

2. The method of managing abdominal stoma prolapse of claim 1, further comprising:
    unseating the distal end of the prosthesis by manually tugging on a part of the prosthesis remaining outside the stoma; and
    withdrawing the prosthesis completely from the stoma by continued manual pulling.

3. An abdominal stoma-prolapse prosthesis, comprising:
    a plastic piece configured as two open rings which are generally parallel to one another:
    each open ring having a plurality of spokes;
    a central stem linking the plurality of spokes of one of said open rings to the plurality of spokes of the other open ring;
    wherein, at least one of the two open rings is collapsible and flexible enough on its spokes to be twisted and inserted through a stoma;
    wherein, the two open rings each have a diameter configured to exceed that of the stoma;
    wherein, the diameter of each of the two open rings is configured to exceed the thickness of an abdominal wall around the stoma; and
    wherein, the abdominal stoma-prolapse prosthesis prevents stoma prolapse with minimal interference to fecal discharge.

4. The abdominal stoma-prolapse prosthesis of claim 3 wherein the plastic piece is biocompatible.

5. The abdominal stoma-prolapse prosthesis of claim 3 wherein the two open rings are coaxial on the central stem.

6. The abdominal stoma-prolapse prosthesis of claim 3 wherein the two open rings are the same diameter.

7. The abdominal stoma-prolapse prosthesis of claim 3 wherein the two open rings are not the same diameter.

8. The abdominal stoma-prolapse prosthesis of claim 3 wherein the diameter of the two open rings is twice the length of the central stem.

9. The abdominal stoma-prolapse prosthesis of claim 3 wherein the diameter of the two open rings is eight times the width of the central stem.

* * * * *